(12) United States Patent  
Bar-El et al.

(10) Patent No.: US 9,037,229 B2
(45) Date of Patent: May 19, 2015

(54) MAGNETIC PATCH COUPLING

(75) Inventors: Yossi Bar-El, Beit Arye (IL); Giora Arbel, Tel Mond (IL)

(73) Assignee: SYNERON MEDICAL LTD, Yokneam Illit (IL)

( * ) Notice: Subject to any disclaimer, the term of this patent is extended or adjusted under 35 U.S.C. 154(b) by 1314 days.

(21) Appl. No.: 12/682,291

(22) PCT Filed: Oct. 12, 2008

(86) PCT No.: PCT/IL2008/001357
§ 371 (c)(1),
(2), (4) Date: Jul. 7, 2010

(87) PCT Pub. No.: WO2009/047774
PCT Pub. Date: Apr. 16, 2009

(65) Prior Publication Data
US 2010/0286588 A1 Nov. 11, 2010

Related U.S. Application Data

(60) Provisional application No. 60/998,368, filed on Oct. 9, 2007.

(51) Int. Cl.
*A61N 1/30* (2006.01)
*A61N 1/32* (2006.01)
*A61N 1/04* (2006.01)

(52) U.S. Cl.
CPC .............. *A61N 1/327* (2013.01); *A61N 1/0424* (2013.01); *A61N 1/044* (2013.01)

(58) Field of Classification Search
USPC ........... 604/20–22, 164.01–170.03, 533–284, 604/174–180
See application file for complete search history.

(56) References Cited

U.S. PATENT DOCUMENTS

| 4,940,456 | A | 7/1990 | Sibalis et al. |
| 5,087,240 | A | 2/1992 | Sibalis |
| 5,158,537 | A | 10/1992 | Haak et al. |
| 5,250,023 | A | 10/1993 | Lee et al. |
| 5,445,609 | A | 8/1995 | Lattin et al. |
| 5,445,611 | A | 8/1995 | Eppstein et al. |
| 5,458,140 | A | 10/1995 | Eppstein et al. |
| 5,498,235 | A | 3/1996 | Flower |

(Continued)

FOREIGN PATENT DOCUMENTS

| WO | WO 94/14062 | 6/1994 |
| WO | WO 96/17651 | 6/1996 |

(Continued)

OTHER PUBLICATIONS

A Supplementary European Search Report dated Apr. 29, 2011, which issued during the prosecution of Applicant's EP 06 75 6211.

(Continued)

*Primary Examiner* — Kevin C Sirmons
*Assistant Examiner* — Phillip Gray
(74) *Attorney, Agent, or Firm* — Smith Risley Tempel Santos LLC; Gregory Scott Smith

(57) ABSTRACT

Apparatus is described for facilitating delivery of a substance through skin (70) of a subject. A skin preparation device (50), and a patch assembly (20) that comprises the substance and is magnetically couplable to the skin preparation device, are described. Other embodiments are also described.

13 Claims, 6 Drawing Sheets

(56) References Cited

U.S. PATENT DOCUMENTS

| | | | |
|---|---|---|---|
| 5,674,191 A | 10/1997 | Edwards et al. | |
| 5,681,282 A | 10/1997 | Eggers et al. | |
| 5,698,217 A | 12/1997 | Wilking | |
| 5,722,397 A | 3/1998 | Eppstein | |
| 5,776,092 A | 7/1998 | Farin et al. | |
| 5,873,855 A | 2/1999 | Eggers et al. | |
| 5,885,211 A | 3/1999 | Eppstein et al. | |
| 5,888,198 A | 3/1999 | Eggers et al. | |
| 5,908,401 A | 6/1999 | Henley | |
| 5,961,482 A | 10/1999 | Chien et al. | |
| 5,983,130 A | 11/1999 | Phipps et al. | |
| 5,983,135 A | 11/1999 | Avrahami | |
| 6,022,316 A | 2/2000 | Eppstein et al. | |
| 6,024,733 A | 2/2000 | Eggers et al. | |
| 6,142,939 A | 11/2000 | Eppstein et al. | |
| 6,148,232 A * | 11/2000 | Avrahami | 604/20 |
| 6,173,202 B1 | 1/2001 | Eppstein et al. | |
| 6,183,434 B1 | 2/2001 | Eppstein | |
| 6,275,728 B1 | 8/2001 | Venkatraman et al. | |
| 6,302,874 B1 | 10/2001 | Zhang et al. | |
| 6,352,506 B1 | 3/2002 | Eppstein et al. | |
| 6,440,121 B1 | 8/2002 | Weber et al. | |
| 6,477,410 B1 | 11/2002 | Henley et al. | |
| 6,490,482 B2 | 12/2002 | Mori et al. | |
| 6,508,785 B1 | 1/2003 | Eppstein | |
| 6,510,341 B1 | 1/2003 | Kuribayashi et al. | |
| 6,527,716 B1 | 3/2003 | Eppstein | |
| 6,530,915 B1 | 3/2003 | Eppstein et al. | |
| 6,595,947 B1 | 7/2003 | Mikszta et al. | |
| 6,597,946 B2 | 7/2003 | Avrahami et al. | |
| 6,611,706 B2 | 8/2003 | Avrahami et al. | |
| 6,611,707 B1 | 8/2003 | Prausnitz et al. | |
| 6,615,079 B1 | 9/2003 | Avrahami | |
| 6,623,454 B1 | 9/2003 | Eggers et al. | |
| 6,632,193 B1 | 10/2003 | Davison et al. | |
| 6,678,554 B1 | 1/2004 | Sun et al. | |
| 6,692,456 B1 | 2/2004 | Eppstein et al. | |
| 6,708,060 B1 | 3/2004 | Avrahami et al. | |
| 6,711,435 B2 | 3/2004 | Avrahami | |
| 6,719,754 B2 | 4/2004 | Underwood et al. | |
| 6,743,211 B1 | 6/2004 | Prausnitz et al. | |
| 6,767,341 B2 | 7/2004 | Cho | |
| 6,773,431 B2 | 8/2004 | Eggers et al. | |
| 6,925,317 B1 * | 8/2005 | Samuels et al. | 600/344 |
| 7,062,317 B2 | 6/2006 | Avrahami et al. | |
| 7,123,957 B2 | 10/2006 | Avrahami | |
| 7,164,942 B2 | 1/2007 | Avrahami et al. | |
| 7,335,377 B2 | 2/2008 | Stern et al. | |
| 7,363,075 B2 | 4/2008 | Stern et al. | |
| 7,383,084 B2 | 6/2008 | Stern et al. | |
| 7,395,111 B2 | 7/2008 | Levin et al. | |
| 7,415,306 B2 | 8/2008 | Levin et al. | |
| 7,435,247 B2 | 10/2008 | Woloszko et al. | |
| 7,494,488 B2 | 2/2009 | Weber | |
| 7,558,625 B2 | 7/2009 | Levin et al. | |
| 7,643,874 B2 | 1/2010 | Nitzan et al. | |
| 2001/0051180 A1 | 12/2001 | Watanabe et al. | |
| 2002/0010412 A1 | 1/2002 | Eppstein | |
| 2002/0010414 A1 | 1/2002 | Coston et al. | |
| 2002/0082543 A1 | 6/2002 | Park et al. | |
| 2002/0091311 A1 | 7/2002 | Eppstein et al. | |
| 2002/0099308 A1 | 7/2002 | Bojan et al. | |
| 2002/0161324 A1 | 10/2002 | Henley et al. | |
| 2002/0169394 A1 | 11/2002 | Eppstein et al. | |
| 2002/0193729 A1 | 12/2002 | Cormier et al. | |
| 2003/0078499 A1 | 4/2003 | Eppstein | |
| 2003/0092982 A1 | 5/2003 | Eppstein | |
| 2004/0039342 A1 | 2/2004 | Eppstein et al. | |
| 2004/0039343 A1 | 2/2004 | Eppstein et al. | |
| 2004/0210214 A1 | 10/2004 | Knowlton | |
| 2005/0049543 A1 | 3/2005 | Anderson et al. | |
| 2005/0119605 A1 | 6/2005 | Sohn | |
| 2005/0203359 A1 | 9/2005 | Blank et al. | |
| 2007/0009542 A1 | 1/2007 | Levin et al. | |
| 2007/0031495 A1 | 2/2007 | Eppstein et al. | |
| 2007/0191827 A1 | 8/2007 | Lischinsky et al. | |
| 2007/0270732 A1 | 11/2007 | Levin et al. | |
| 2007/0287949 A1 | 12/2007 | Levin et al. | |
| 2007/0292445 A1 | 12/2007 | Levin | |
| 2008/0114281 A1 | 5/2008 | Birchall et al. | |
| 2008/0208107 A1 | 8/2008 | McRae et al. | |
| 2008/0214986 A1 | 9/2008 | Ivorra et al. | |
| 2008/0214988 A1 | 9/2008 | Altshuler et al. | |
| 2008/0274166 A1 | 11/2008 | Sacks et al. | |
| 2009/0105706 A1 | 4/2009 | Livneh | |
| 2009/0264810 A1 | 10/2009 | Eppstein et al. | |
| 2010/0174224 A1 | 7/2010 | Sohn | |
| 2010/0293807 A1 | 11/2010 | Bar-El et al. | |
| 2012/0022435 A1 | 1/2012 | Ignon et al. | |
| 2012/0022504 A1 | 1/2012 | Epshtein et al. | |

FOREIGN PATENT DOCUMENTS

| | | |
|---|---|---|
| WO | WO 96/40364 | 12/1996 |
| WO | WO 97/07734 | 3/1997 |
| WO | WO 97/16222 | 5/1997 |
| WO | WO 98/00193 | 1/1998 |
| WO | WO 98/29134 | 7/1998 |
| WO | WO 99/44507 | 9/1999 |
| WO | WO 99/44508 | 9/1999 |
| WO | WO 99/44637 | 9/1999 |
| WO | WO 99/44638 | 9/1999 |
| WO | WO 99/44678 | 9/1999 |
| WO | WO 00/03758 | 1/2000 |
| WO | WO 00/04832 | 2/2000 |
| WO | WO 00/15102 | 3/2000 |
| WO | WO 00/59371 | 10/2000 |
| WO | WO 00/74583 | 12/2000 |
| WO | WO 00/74767 | 12/2000 |
| WO | WO 00/076575 | 12/2000 |
| WO | WO 00/76575 | 12/2000 |
| WO | WO 01/35820 | 5/2001 |
| WO | WO 02/090210 | 11/2002 |
| WO | WO 03/039620 | 5/2003 |
| WO | WO 03/077970 | 9/2003 |
| WO | WO 03/077971 | 9/2003 |
| WO | WO 03/101507 | 12/2003 |
| WO | 2006/131931 A2 | 12/2006 |
| WO | WO 06/131931 | 12/2006 |
| WO | WO 2006/131931 | 12/2006 |
| WO | WO 2008/091878 | 7/2008 |
| WO | WO 09/047774 | 4/2009 |
| WO | WO 2009/047774 | 4/2009 |

OTHER PUBLICATIONS

European Search Report dated Apr. 7, 2011, which issued during the prosecution of Applicant's EP 11 00 0062.

An Examination Report dated Apr. 6, 2011, which issued during the prosecution of Applicant's EP 99952784.9.

A Supplementary European Search Report dated Feb. 28, 2011, which issued during the prosecution of Applicant's European Patent Application No. 08837792.

An International Search Report dated Feb. 17, 2009, which issued during the prosecution of Applicant's PCT/IL2008/001357.

* cited by examiner

MAGNETIC PATCH COUPLING

CROSS-REFERENCES TO RELATED APPLICATIONS

The present application is a U.S. national phase of PCT Application No. PCT/IL2008/001357 to Bar-El et al., filed Oct. 12, 2008, which claims the benefit of U.S. Provisional Patent Application 60/998,368 to Bar-El et al., filed Oct. 9, 2007, entitled, "Magnetic patch coupling," which is incorporated herein by reference.

FIELD OF THE INVENTION

The present invention relates generally to methods and devices for drug delivery and specifically to methods and devices for transdermal drug delivery.

BACKGROUND OF THE INVENTION

Adhesive transdermal drug patches deliver a drug across the skin directly into the systemic blood circulation. Typically, the drug is dispersed in the adhesive that attaches the patch to the skin.

PCT Publication WO 2003/039620 to Sohn, which is incorporated herein by reference, describes apparatus for facilitating delivery of a substance through skin of a subject. The apparatus includes a handle and a cartridge, removably coupled to the handle. The cartridge includes one or more electrodes and a patch comprising the substance, the electrodes adapted to be applied to a region of the skin, and the patch adapted to be applied to at least a portion of the region of the skin by removal of the electrodes therefrom.

PCT Publication WO 2006/131931 to Sacks et al., which is incorporated herein by reference, describes apparatus including a transdermal drug delivery patch product, which includes a patch, which includes a drug; and protective packaging, adapted to store the patch, and to allow the drug to dry while the patch is stored in the protective packaging. Other embodiments are also described.

U.S. Pat. No. 6,148,232 to Avrahami, which is incorporated herein by reference, described a device for ablating the stratum corneum epidermidis of a subject, including a plurality of electrodes, which are applied to the subject's skin at respective points. A power source applies electrical energy between two or more of the plurality of electrodes, in order to cause ablation of the stratum corneum primarily in an area intermediate the respective points.

PCT Publication WO 00/76575 to Samuels et al., relevant portions of which are incorporated herein by reference, describes an alignment device and related systems and methods for aligning at least one apparatus with respect to a surface of a tissue. The alignment device is described as comprising a tissue interface member suitable for positioning on the surface of the tissue and mating with the apparatus to maintain alignment of the apparatus during an operation of the apparatus. The alignment device is described as being useful in aligning various apparatus that are part of a continuous analyte monitoring system. The '575 application states that the tissue interface member can have additional structural features that facilitate mating with an apparatus. Examples of such characteristics include, but are not limited to, complementary magnetic surface portions, adhesive on engaging surfaces, and/or complementary male or female members.

SUMMARY OF THE INVENTION

In some embodiments of the invention, a skin preparation device that is configured to facilitate delivery of a substance such as a drug through the skin of a subject is magnetically coupled to a patch assembly that contains the substance. Typically, the skin preparation device comprises one or more electrodes configured to ablate the skin.

For some applications, the patch assembly comprises a first portion and a second portion foldably coupled to the first portion. Typically, the first portion comprises a frame that surrounds at least in part an open portion of the patch assembly, such that a region of the skin is exposed through the open portion when the first portion is placed on the skin. The second portion comprises a pad that contains the substance, the pad being adapted to be brought into contact, through the open portion, with the skin.

In some embodiments, one or more magnets are coupled to the patch assembly, the one or more magnets being configured to couple the patch assembly to the skin preparation device when the patch assembly is aligned with the skin preparation device. Typically, the magnets are configured not to couple the patch assembly to the skin preparation device when the patch assembly is not aligned with the skin preparation device.

In some embodiments, the patch assembly comprises a rectangular portion having long sides and short sides thereof, and the distal end of the skin preparation device is rectangular having long sides and short sides thereof. The magnets are configured to couple the patch assembly to the skin preparation device when the long sides of the distal end of the skin preparation device are aligned with the long sides of the rectangular portion of the patch assembly. For some applications, the one or more magnets comprise four magnets, and each of the four magnets is coupled to a respective corner of the rectangular portion of the patch assembly.

In some embodiments, the skin preparation device is coupled to the patch assembly, following which the patch assembly is adhered to the skin. The skin is prepared for delivery of the substance by activating the skin preparation device, and a portion of the patch assembly that includes the substance is applied to the skin. For some applications, the patch assembly is adhered to the skin by applying the skin preparation device to the skin subsequent to the coupling of the skin preparation device to the patch assembly. In some embodiments, the skin preparation device is removed from the skin, which leaves a first portion of the patch assembly adhered to the skin, and removes a second portion of the patch assembly from the first portion.

There is therefore provided, in accordance with an embodiment of the invention, apparatus for facilitating delivery of a substance through skin of a subject, including:

a skin preparation device; and a patch assembly including the substance and magnetically couplable to the skin preparation device.

In an embodiment, the skin preparation device includes one or more electrodes configured to ablate the skin.

In an embodiment, the patch assembly includes a first portion and a second portion foldably coupled to the first portion.

In an embodiment:

the first portion includes a frame that surrounds at least in part an open portion of the patch assembly, such that a region of the skin is exposed through the open portion when the first portion is placed on the skin, and the second portion includes a pad including the substance, the pad being adapted to be brought into contact, through the open portion, with at least a portion of the region of the skin.

In an embodiment, the apparatus further includes one or more patch magnets coupled to the patch assembly, and the one or more patch magnets are configured to couple the patch assembly to the skin preparation device when the patch assembly is aligned with the skin preparation device.

In an embodiment, the skin preparation device includes a magnetic material (e.g., a ferromagnetic material or a paramagnetic material), and the one or more patch magnets are configured to magnetically couple the patch assembly to the skin preparation device via the magnetic material.

In an embodiment, a distal end of the skin preparation device includes one or more device magnets, and the one or more patch magnets are configured to couple the patch assembly to the skin preparation device via the device magnets.

In an embodiment, the patch magnets are configured not to couple the patch assembly to the skin preparation device when the patch assembly is not aligned with the skin preparation device.

In an embodiment,
the patch assembly includes a frame that surrounds an open portion,
the patch magnets are configured to couple the patch assembly to the skin preparation device when the distal end of the skin preparation device is placed near the open portion, and
the distal end of the skin preparation device is configured to be inserted through the open portion.

In an embodiment,
the patch assembly includes a rectangular portion having long sides and short sides thereof,
a distal end of the skin preparation device is rectangular having long sides and short sides thereof, and
the patch magnets are configured to couple the patch assembly to the skin preparation device when the long sides of the distal end of the skin preparation device are aligned with the long sides of the rectangular portion of the patch assembly.

In an embodiment, the patch magnets are configured not to couple the patch assembly to the skin preparation device when the long sides of the distal end of the skin preparation device are not aligned with the long sides of the rectangular portion of the patch assembly.

In an embodiment, the one or more patch magnets include four magnets, and each of the four magnets is coupled to a respective corner of the rectangular portion of the patch assembly.

In an embodiment, the patch magnets are configured to couple the patch assembly to the skin preparation device when the long sides of the distal end of the skin preparation device are aligned with the long sides of the rectangular portion of the patch assembly in a first direction, and the magnets are configured not to couple the patch assembly to the skin preparation device when the long sides of the distal end of the skin preparation device are aligned with the long sides of the rectangular portion of the patch assembly in a second direction opposite to the first direction.

In an embodiment, the skin preparation device is configured to be magnetically coupled to the patch assembly while the skin preparation device is applied to the skin during a skin preparation treatment.

In an embodiment, the skin preparation device is configured to adhere the patch assembly to the skin.

In an embodiment, the skin preparation device, by being removed from the skin subsequent to the skin preparation treatment, is configured to:
leave a first portion of the patch assembly adhered to the skin; and
remove a second portion of the patch assembly from the first portion.

There is also provided, in accordance with an embodiment of the invention, a method for facilitating delivery of a substance through skin of a subject, including:
magnetically coupling a skin preparation device to a patch assembly;
adhering the patch assembly to the skin;
preparing the skin for delivery of the substance by activating the skin preparation device; and
applying to the skin a portion of the patch assembly that includes the substance.

The present invention will be more fully understood from the following detailed description of embodiments thereof, taken together with the drawings, in which:

DETAILED DESCRIPTION OF EMBODIMENTS

Figure 1:
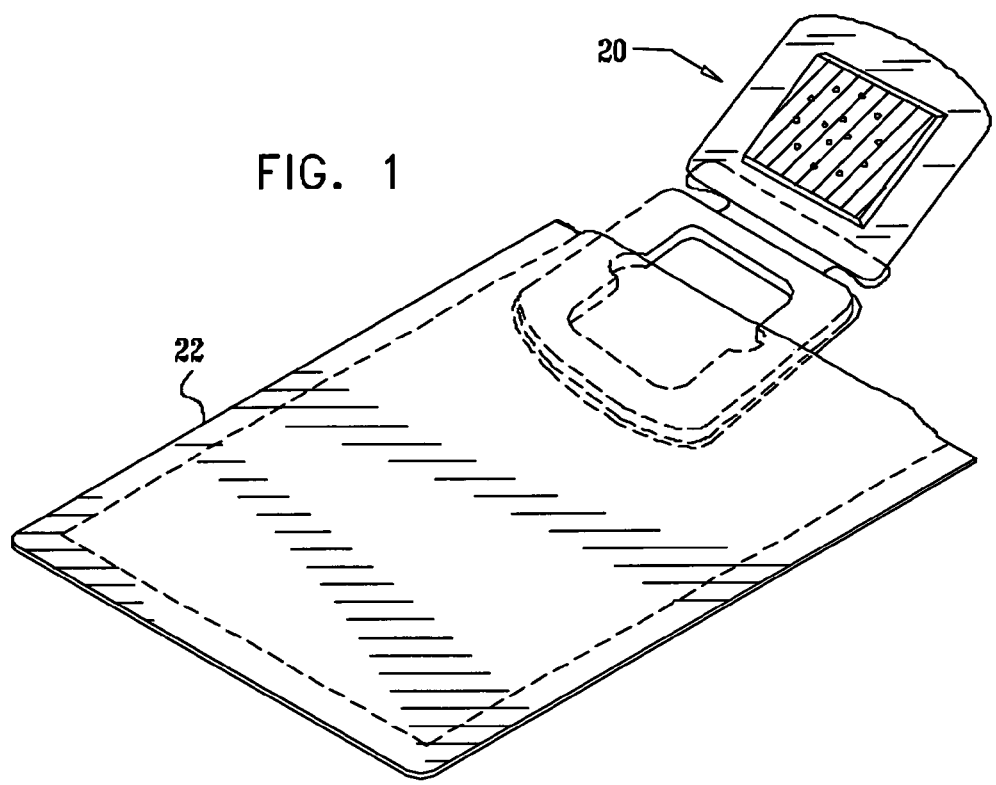
FIG. 1 is a schematic illustration of a patch assembly, in accordance with an embodiment of the present invention.
Figure 2:
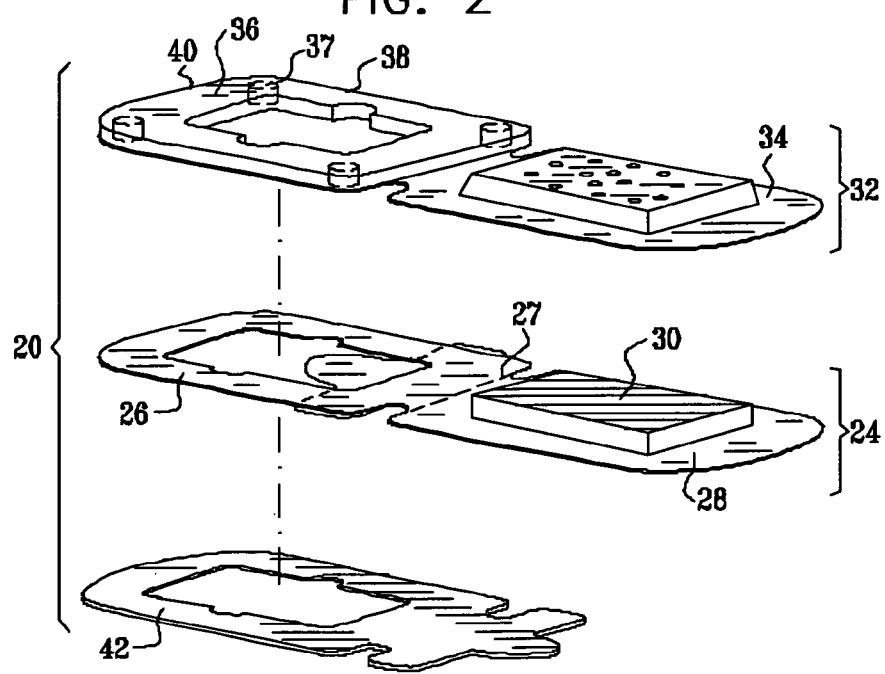
FIG. 2 is a schematic illustration of layers of the patch assembly, in accordance with an embodiment of the present invention.

Reference is now made to FIGS. 1 and 2, which are schematic illustrations of a patch assembly 20, in accordance with an embodiment of the present invention. The patch is typically stored inside packaging 22. Except as described hereinbelow, patch assembly 20 is generally similar to patch 120 described in PCT Publication WO 2006/131931 cited hereinabove. Patch 20 is configured to deliver a substance, typically a drug, through the skin of a subject.

Patch assembly 20 comprises a support structure 24, which is shaped to define a window area 26 and a drug support area 28. The window area and the drug support area are foldably coupled to each other along fold 27. The drug support area supports a drug delivery area 30. For example, drug delivery area may comprise a medicated pad, and/or a drug directly adhered to drug support area 28.

Patch assembly 20 comprises a top liner 32, which is shaped to define a liner window area 36 and a protective area 34. Typically, liner window area 36 comprises one or more magnets 37 which are configured to couple the patch assembly to a skin preparation device, as described in further detail hereinbelow. In some embodiments, liner window area 36 comprises four magnets, each of the four magnets disposed at a respective corner of the window area and typically embedded in the body of liner window area 36.

Patch assembly 20 further comprises a bottom liner 42 which is configured to be removably coupled to a lower surface of window area 26.

Typically, window area 26 and, correspondingly, liner window area 36, is rectangular, comprising long sides 38 and short sides 40 thereof. In some embodiments, window area 26 may be other shapes, such as square, elliptical, or circular, in which case drug delivery area 30 is also typically a corresponding other shape.

Figure 3A:
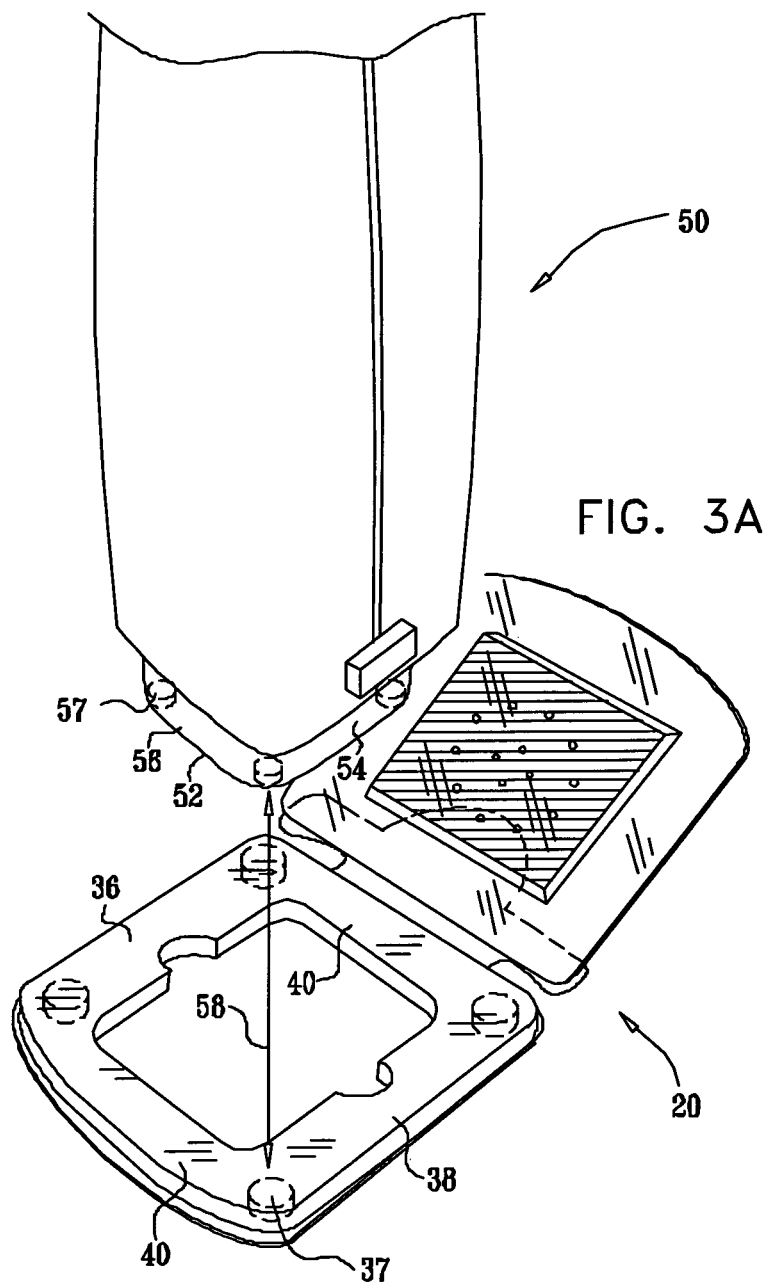
FIGS. 3A and 3B are schematic illustrations of the patch assembly being magnetically coupled to a skin preparation device, in accordance with an embodiment of the present invention.
Figure 3B:
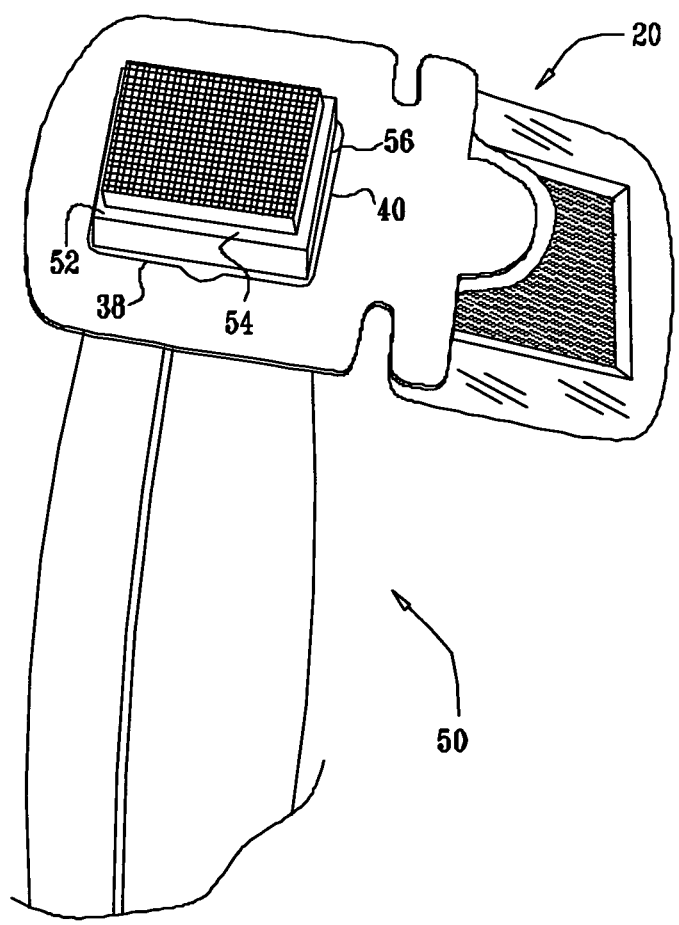

Reference is now made to FIGS. 3A and 3B, which are schematic illustrations of a skin preparation device 50 being magnetically coupled to patch assembly 20, in accordance with an embodiment of the present invention. Typically, a distal end 52 of the skin preparation device is aligned with the patch assembly, as shown in FIG. 3A. The one or more magnets 37 of window area 36 of the patch assembly are configured to magnetically couple the skin preparation device to the patch assembly when they are correctly aligned and sufficiently close to each other, as shown by magnetic force arrow 58 in FIG. 3A.

In some embodiments, skin preparation device 50 comprises a magnetic material (for example, iron, cobalt and/or nickel), and is configured to passively couple with the one or more magnets 37 of window area 36. Alternatively or additionally, distal end 52 of the skin preparation device comprises one or more magnets 57, which are typically embedded in the body of the device, and liner window area 36 comprises magnets 37 or a magnetic material.

Typically, one or more magnets 37 of liner window area 36 are configured not to couple skin preparation device 50 to patch assembly 20 when the skin preparation device and the patch assembly are not aligned. For example, indication lights, LEDs, and/or an LCD display may be disposed on one side of the skin preparation device. The magnets may be configured not to couple the skin preparation device to the patch assembly when the device is not aligned with the patch assembly in such a way that the lights, LED, and/or LCD display are in the line of sight of the subject.

In some embodiments, distal end 52 of skin preparation device 50 is shaped to define long sides 54 and short sides 56 thereof. The magnets are configured to couple the skin preparation device to the patch when the long sides 54 of the distal end of the skin preparation device are aligned with the long sides 38 of the patch assembly.

In some embodiments, one or more magnets 37 of window area 36 are configured to couple the skin preparation device to the patch when long sides 54 of distal end 52 of skin preparation device 50 are aligned with the long sides 38 of patch assembly 20 in a first direction, but not when the long sides of the distal end of the skin preparation device are aligned with the long sides of the patch assembly in a second direction that is opposite to the first direction. For example, when the patch and the skin preparation device are arranged as shown in FIG. 3A, the magnets may be configured to couple the skin preparation device to the patch. When the patch is rotated by 180 degrees, in the plane of the paper, so that the long sides of device 50 are aligned with the long sides of the patch assembly, but in the opposite direction, the magnets are configured not to couple device 50 to the patch assembly.

It is noted that although some embodiments are described herein with respect to forcing coupling of the skin preparation device to the patch assembly in only a certain angular alignment, the scope of the present invention includes allowing the skin preparation device to be coupled to the patch assembly in any angular alignment.

Figure 4:
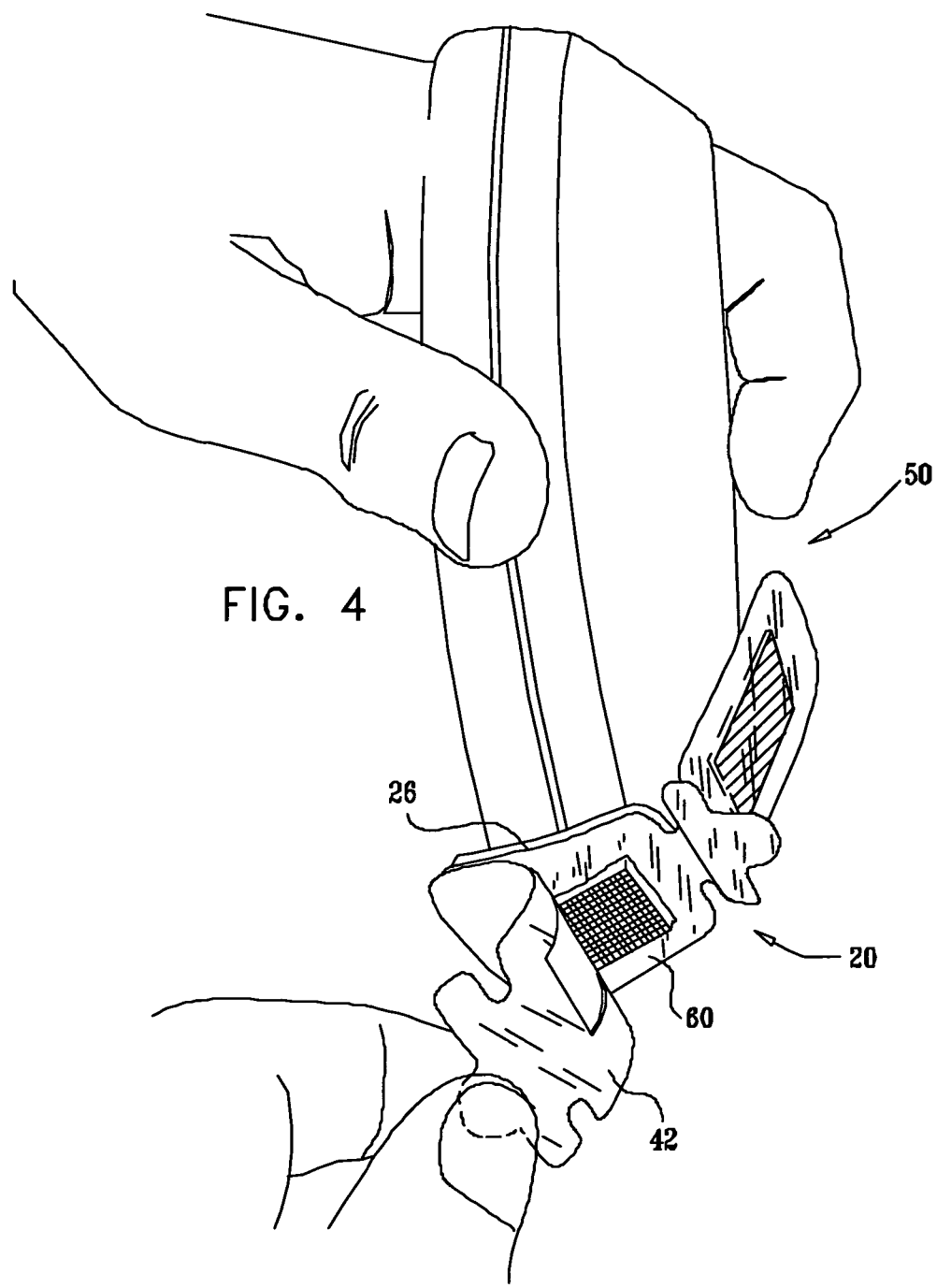
FIG. 4 is a schematic illustration of the patch assembly being prepared for adhesion to a subject's skin, in accordance with an embodiment of the present invention.

Reference is now made to FIG. 4, which is a schematic illustration of bottom liner 42 being removed from a bottom surface 60 of window area 26 of patch assembly 20. The bottom liner is typically removed from the window area of the patch assembly subsequent to the magnetic coupling of the patch assembly to skin preparation device 50. Typically, bottom surface 60 of window area 26 of patch assembly 20 is adhesive and is configured to be adhered to the subject's skin. Further typically, window area 26 is coupled to, or comprises, a rigid rim configured to dissipate evenly a force applied thereto. By evenly dissipating the force the rigid rim adheres bottom surface 60 evenly to the subject's skin.

Figure 5:
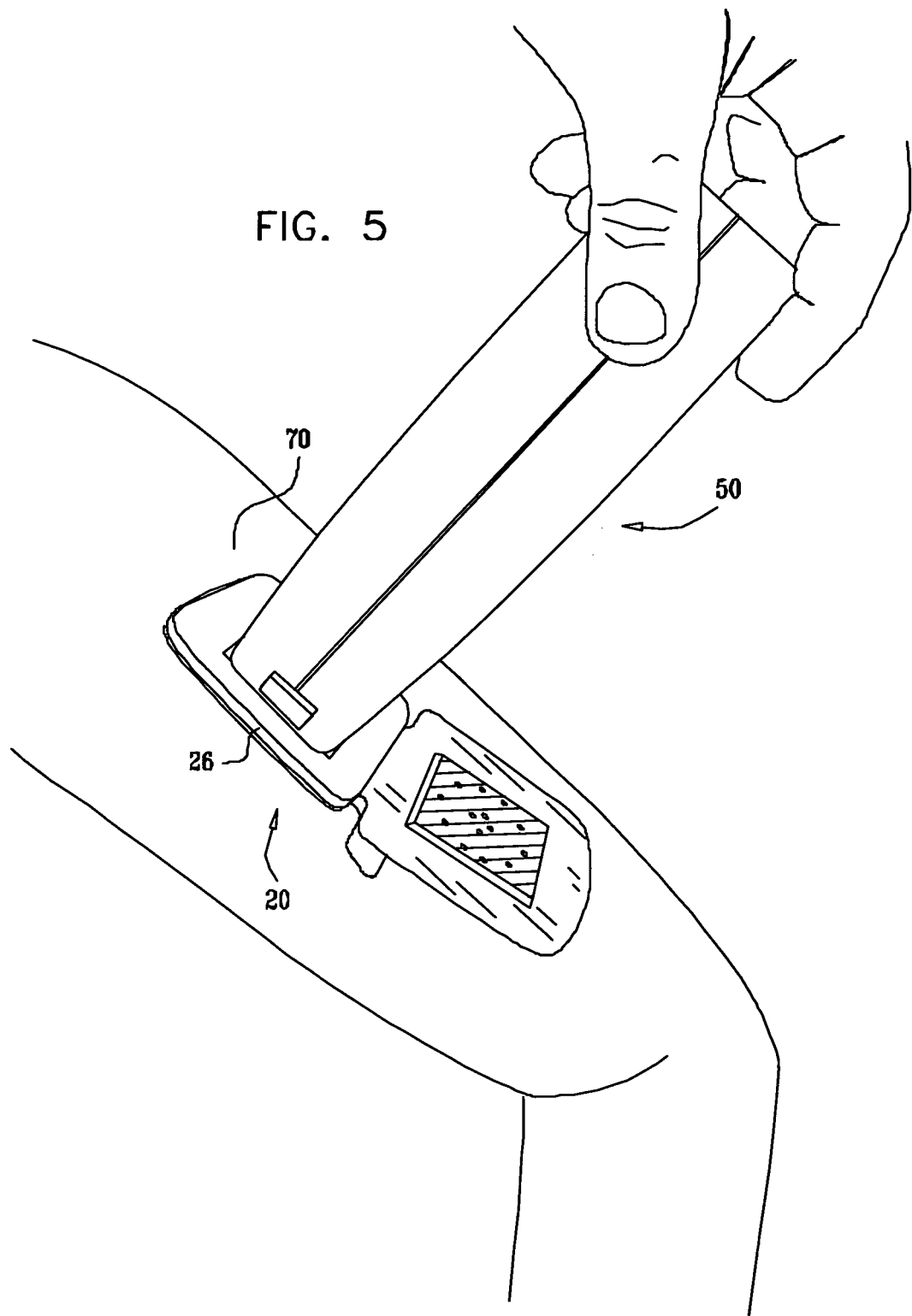
FIG. 5 is a schematic illustration of the skin preparation device being applied to the subject's skin, in accordance with an embodiment of the present invention.

Reference is now made to FIG. 5, which is a schematic illustration of skin preparation device 50 being applied to the subject's skin 70, in accordance with an embodiment of the present invention. In some embodiments, the skin preparation device prepares the skin for delivery of a drug from patch assembly 20, by ablating the skin, the skin preparation device comprising ablating electrodes. Typically, bottom surface 60 of window area 26 of patch assembly 20 is adhesive and the skin preparation device is configured to adhere the patch assembly to the skin of the subject by being applied to the skin.

Figure 6A:
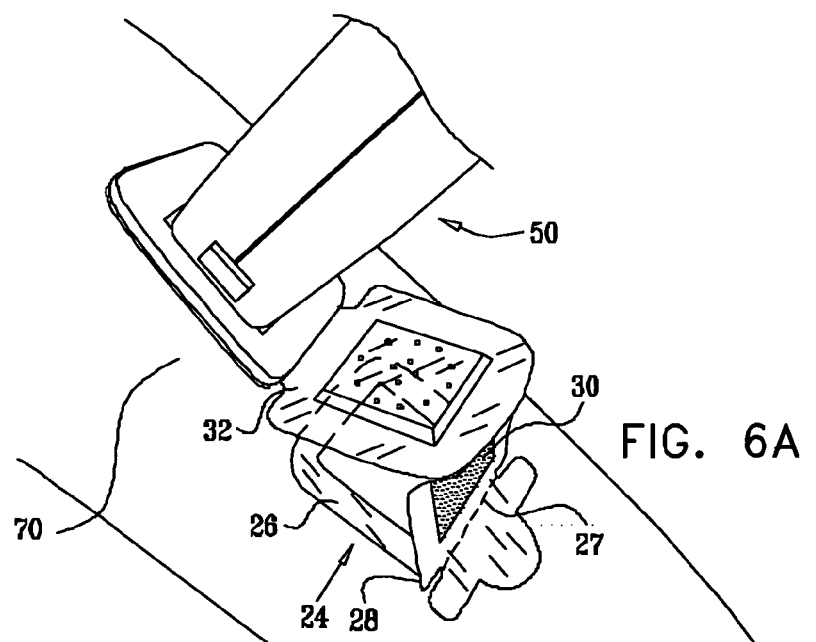
FIGS. 6A and 6B are schematic illustrations of a drug delivery portion of the patch assembly being coupled to the subject's skin, in accordance with an embodiment of the present invention.
Figure 6B:
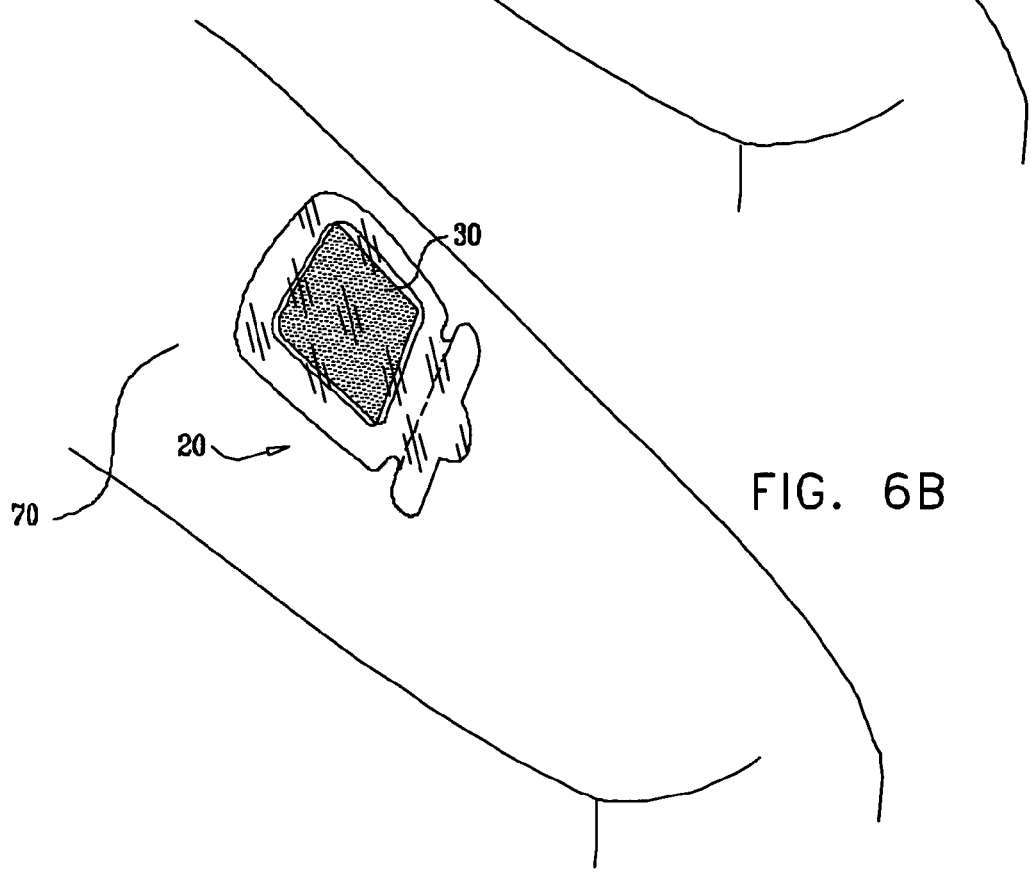

Reference is now made to FIGS. 6A and 6B, which are schematic illustrations of drug delivery area 30 of patch assembly 20 being coupled to a subject's skin 70, in accordance with an embodiment of the present invention. Skin preparation device 50 is removed from the subject's skin, as shown in FIG. 6A. Window area 26 of the patch assembly remains adhered to the subject's skin. Top liner 32 of the patch assembly is magnetically coupled to the skin preparation device and is removed from support structure 24 of the patch assembly. In some embodiments, top liner 32 is coated with silicon and is more strongly coupled to the skin preparation device than to drug support area 28; therefore, the top liner is removed from the support structure when the skin preparation device is removed from the subject's skin.

Typically, as shown in FIG. 6A, as top liner 32 is removed from support structure 24, drug support area 28 is folded over fold 27. Drug delivery area 30 becomes coupled to the subject's skin 70, as shown in FIG. 6B. Alternatively or additionally, drug support area 28 is manually folded over fold 27, and/or drug delivery area 30 is manually coupled to the subject's skin.

Although some embodiments of the present invention are described herein with respect to delivery of a substance into the skin, the scope of the present invention includes using techniques described herein for analyte extraction, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for facilitating the delivery of a substance through the skin of a subject, comprising:
   a patch assembly comprising:
      a support structure and a drug support area, wherein the support structure and the drug support area are coupled to each other along a single edge such that the drug support area and is configured to be folded over the support structure along the single edge, the drug support area including a drug delivery area and the support structure defining a window area and having a lower surface that adheres to a surface of skin and an upper surface, wherein when the drug support area is folded over the support structure, the drug delivery area corresponds with the window area; and
      a top liner configured to be positioned over the upper surface of the support structure and the drug support area, the top liner defining a top liner window area including one or more magnets and a protective area; and a skin preparation device that is configured to be magnetically coupled to the one or more magnets of the top liner window area when the skin preparation device is applied to the skin through the window area of the support structure, so as to facilitate a skin preparation treatment; and wherein upon removal of the skin preparation device from the skin, the top liner, which is magnetically coupled to the skin preparation device, is automatically removed from the support structure and the drug support area of the patch assembly, the support structure remains adhered to the surface of skin, and such removal causes the drug support area to be folded along the single edge over the support structure window area and the drug delivery area becomes coupled to the skin through the window area of the support structure.

2. The apparatus according to claim 1, wherein the top liner is coated with silicone.

3. The apparatus according to claim 1, wherein the skin preparation device comprises one or more electrodes configured to ablate the skin.

4. The apparatus according to claim 1, wherein:
the support structure window area is defined by a frame that surrounds at least in part an open portion of the patch assembly, such that a region of the skin is exposed through the open portion when the patch is placed on the skin, and wherein the drug support area comprises a pad comprising a substance, the pad being adapted to be brought into contact, through the open portion, with at least a portion of the region of the skin.

5. The apparatus according to claim 1, further comprising one or more patch magnets coupled to the patch assembly, wherein the one or more patch magnets are configured to couple the patch assembly to the skin preparation device when the patch assembly is aligned with the skin preparation device.

6. The apparatus according to claim 5, wherein the skin preparation device comprises a magnetic material and wherein the one or more patch magnets are configured to magnetically couple the patch assembly to the skin preparation device via the magnetic material.

7. The apparatus according to claim 5, wherein a distal end of the skin preparation device comprises one or more device magnets, and wherein the one or more patch magnets are configured to couple the patch assembly to the skin preparation device via the device magnets.

8. The apparatus according to claim 5, wherein the patch magnets are configured not to couple the patch assembly to the skin preparation device when the patch assembly is not aligned with the skin preparation device.

9. The apparatus according to claim 5, wherein the patch assembly comprises a frame that surrounds an open portion, wherein the patch magnets are configured to couple the patch assembly to the skin preparation device when the distal end of the skin preparation device is placed near the open portion, and wherein the distal end of the skin preparation device is configured to be inserted through the open portion.

10. The apparatus according to claim 5, wherein the patch assembly comprises a rectangular portion having long sides and short sides thereof, wherein a distal end of the skin preparation device is rectangular having long sides and short sides thereof, and wherein the patch magnets are configured to couple the patch assembly to the skin preparation device when the long sides of the distal end of the skin preparation device are aligned with the long sides of the rectangular portion of the patch assembly.

11. The apparatus according to claim 10, wherein the patch magnets are configured not to couple the patch assembly to the skin preparation device when the long sides of the distal end of the skin preparation device are not aligned with the long sides of the rectangular portion of the patch assembly.

12. The apparatus according to claim 10, wherein the one or more patch magnets comprise four magnets, and wherein each of the four magnets is coupled to a respective corner of the rectangular portion of the patch assembly.

13. The apparatus according to claim 10, wherein the patch magnets are configured to couple the patch assembly to the skin preparation device when the long sides of the distal end of the skin preparation device are aligned with the long sides of the rectangular portion of the patch assembly in a first direction, and wherein the magnets are configured not to couple the patch assembly to the skin preparation device when the long sides of the distal end of the skin preparation device are aligned with the long sides of the rectangular portion of the patch assembly in a second direction opposite to the first direction.

* * * * *